US00PP17201P3

(12) United States Plant Patent

Nicolai

(10) Patent No.: US PP17,201 P3
(45) Date of Patent: Nov. 14, 2006

(54) APPLE TREE NAMED 'NICOTER'

(50) Latin Name: *Malus communis Mill.*
Varietal Denomination: Nicoter

(75) Inventor: Johan Nicolai, Sint-Truiden (BE)

(73) Assignee: Better3Fruit N.V., Heverlee (BE)

( * ) Notice: Subject to any disclaimer, the term of this patent is extended or adjusted under 35 U.S.C. 154(b) by 184 days.

(21) Appl. No.: 10/293,207

(22) Filed: Nov. 12, 2002

(65) Prior Publication Data

US 2003/0121084 P1 Jun. 26, 2003

Related U.S. Application Data

(60) Provisional application No. 60/337,600, filed on Nov. 13, 2001.

(51) Int. Cl.
*A01H 5/00* (2006.01)

(52) U.S. Cl. ..... Plt./161

(58) Field of Classification Search ..... Plt./161
See application file for complete search history.

(56) References Cited

PUBLICATIONS

Corresponding Australian PBR Application No. 2004/319 filed Dec. 23, 2004.

Corresponding Swiss PBR Application No. 04–2179 filed Dec. 21, 2004.

*Primary Examiner*—Bruce R. Campell
*Assistant Examiner*—S. B. McCormick-Ewoldt
(74) *Attorney, Agent, or Firm*—Foley & Lardner, LLP

(57) ABSTRACT

A new and distinct apple tree named 'Nicoter'. The new variety is the result of a cross between 'Gala' and 'Braeburn,' and is most similar in appearance to 'Gala'. The new variety is distinguishable from 'Gala' by its red coloration and slightly less conical shape.

1 Drawing Sheet

Latin name of the genus and species of the plant claimed: *Malus communis Mill.*
Variety denomination: 'Nicoter'.

BACKGROUND OF THE INVENTION

The present invention relates to a new and distinct cultivar of apple tree, botanically known as *Malus communis Mill.* and hereinafter referred to by the name 'Nicoter'. This new and distinct cultivar was bred by inventor, Johan Nicolai, in Sint-Truiden, Belgium.

'Nicoter' originated as a controlled cross between 'Gala' (unpatented) and 'Braeburn' (unpatented). It most closely resembles 'Gala' in appearance, although fruit of 'Nicoter' is less conical in shape than that of 'Gala', and the coloration of 'Nicoter' is more pink and less red than 'Gala'. Additional differences are shown in the table below.

| Characteristic | 'Nicoter' | 'Gala' | 'Braeburn' |
|---|---|---|---|
| Fruit Skin color (background) | Yellow | Yellow | Green |
| Overcolor of fruit | Red, pink | Orange red to bright red, striped | Red, striped |
| Flesh Color | Grey, slightly brown | Red brown | Red brown |

The new variety 'Nicoter' has been asexually propagated by T-budding and bench grafting onto 'M9' and 'MM111' rootstocks in Sint-Truiden, Belgium, and has demonstrated that the combination of characteristics as herein disclosed for the new variety are firmly fixed and remain true to type through successive generations of asexual reproduction.

BRIEF DESCRIPTION OF THE PHOTOGRAPH

The FIGURE illustrates the fruit of the new variety, 'Nicoter.'

DETAILED DESCRIPTION OF THE VARIETY

The following is a detailed botanical description of the new and distinct variety of apple tree, based on observations of specimens grown in Sint-Truiden, Belgium. The observed plants are four years old. Colors are described according to The Royal Horticultural Society Colour Chart (R.H.S.), except where general colors of ordinary significance are used It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants of the new variety may vary from the stated average.

All trees of 'Nicoter', insofar as they have been observed, have been identical in all the characteristics described below.

Parentage: 'Gala' (unpatented) and 'Braeburn' (unpatented).
Classification:
*Botanical.*—*Malus communis Mill.*
Propagation: Holds to distinguishing characteristics through succeeding asexual propagations by T-budding and bench grafting onto 'M9' and 'MM111' rootstocks.
*Locality where grown and observed.*—Sint-Truiden, Belgium.
Tree:
*Age.*—Observed plants were four years old.
*Vigor.*—Medium (compare to 'Golden Delicious').

*Trunk diameter.*—35 mm to 50 cm above union.
*Height.*—3.0 m.
*Number of lateral branches.*—12.
*Length of lateral branches.*—Approximately 1.0 m total length.
*Bark color.*—Brown, RHS N200B.
*Branch diameter.*—11 mm.
*Branch color.*—Brown, RHS N200B.
*Lenticels.*—Round and elongated, 1–1.5 mm.

Leaves:
*Leaf length.*—104 mm.
*Leaf width.*—66 mm.
*Leaf margin.*—Irregular, every 2–3 mm, more sharp than round.
*Leaf color* (*based on mature leaf*) Upper surface — green, shiny, RHS 137A. Lower surface — pale green, RHS 138B.
*Leaf texture.*—Slightly hairy.
*Leaf shape.*—Apex: Obtuse; Base: Truncate.
*Petiole length.*—30 mm.
*Petiole color* (*based on mature leaf*).—Green, RHS 142B.
*Vein color.*—Green, RHS 138B.
*Venation pattern.*—Pinnate.
*Stipules.*—Relatively wide, 3 mm wide, 15 mm long.

Flowers:
*Bud length.*—About 8.75 mm±0.81 mm.
*Bud diameter.*—About 4.28 mm±0.33 mm.
*Bud color.*—Greyed-red, RHS 178B.
*Petal number.*—5.
*Petal length.*—22.99 mm±1.68 mm.
*Petal width.*—13.48 mm±1.81 mm.
*Petal color* (*determined on an open flower*).—Upper surface — white, RHS N155B. Lower surface — red-purple, RHS 63C.
*Petal color* (*determined at balloon stage*).—Red-purple, RHS 63B.
*Petal margin.*—Smooth.
*Petal texture.*—Smooth.
*Flower diameter.*—38.57 mm±6.47 mm.

Fruit:
*Fruit average weight.*—201 g.
*Fruit shape.*—Short globose conical (compare to 'Fortune').
*Fruit size.*—Height: 66 mm; Width: 73 mm.
*Stem length.*—17 mm.
*Depth of stem basin.*—23 mm.
*Calyx.*—Depth: 6 mm; Width: 23 mm.
*Overcolor of skin.*—Red, RHS 42B.
*Background color of skin.*—Yellow, RHS 10B, ('Gala' F4).
*Lenticels.*—White, RHS N155A, ± 0.5 mm diameter, Approximately 10 lenticels/cm$^2$.
*Flesh color.*—Yellow, RHS 10D.
*Seeds.*—Present.
*Seed color.*—Grey-orange, RHS 175A.
*Seed length.*—9.42 mm±0.48 mm.
*Seed number.*—7.18±2.30.
*Time of fruit ripening for eating.*—Late (compare to 'Golden Delicious').
*Time of flowering.*—Medium (begins at about the same time as 'Cox's Orange Pippin').
*Sensitivity to pests/disease.*—Susceptible to apple scab (*Venturia inaequalis*).
*Winter hardiness.*—No problems observed during the winter climates of Northwest Europe and the Alps.
*Drought/heat tolerance.*—Good; a yellow blush appears in hot dry climates.
*Market use.*—Fresh market. Excellent dessert apple.
*Shipping/storage characteristics.*—Not sensitive to bruising; very good storability under ULO-conditions (1° C., 2% $O_2$, 2% $CO_2$) for up to 10 months.

Reproductive organs:
*Stamen length.*—8.22 mm±1.72 mm.
*Stamen quantity.*—18.3±2.0.
*Stamen color.*—White, RHS 155C.
*Pollen color* (*color of mature pollen grains was determined*).—Yellow, RHS 4C.
*Pollination requirements.*—Everest, Professor Sprenger, Golden Hornet, Idared, Granny Smith.
*Sepal length.*—7.49 mm±1.21 mm.
*Sepal width.*—4.44 mm±0.55 mm.
*Sepal quantity.*—5.
*Sepal color.*—Green, RHS 143B.
*Pistil length* (*total length determined by measuring length of the part where the pistils are attached together and the length of the part where they are separated*).—12.12 mm±1.16 mm.
*Pistil width* (*width was measured at the base of the pistil*).—0.88±0.14 mm.
*Pistil quantity.*—5.
*Pistil color.*—Yellow-green, RHS 151C.

I claim:

1. A new and distinct apple tree plant named 'Nicoter', substantially as illustrated and described herein.

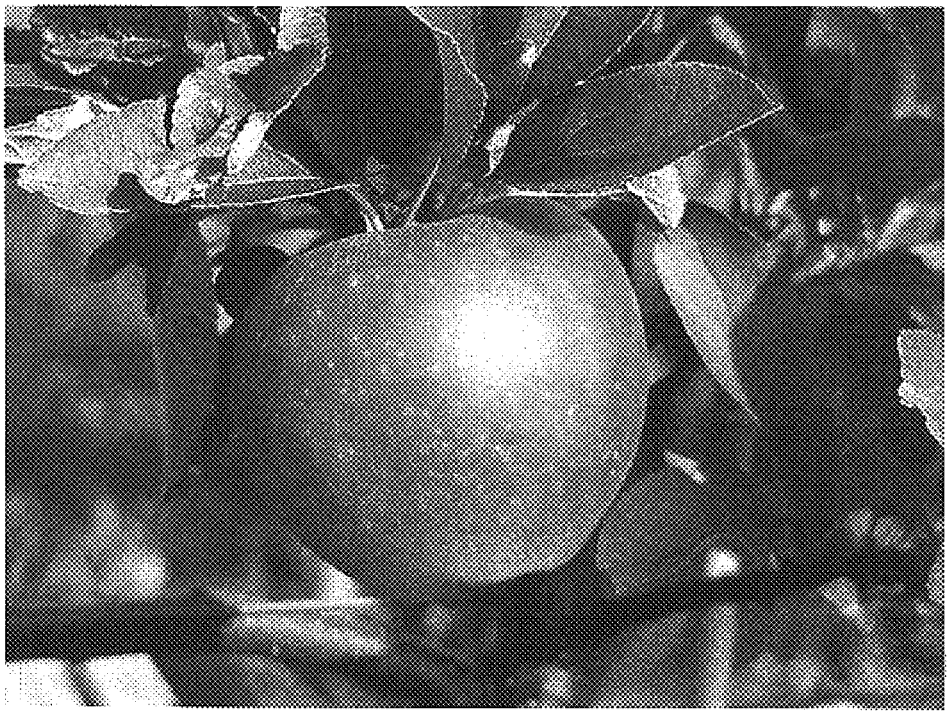

* * * * *